United States Patent [19]

Erickson

[11] 4,192,071
[45] Mar. 11, 1980

[54] DENTAL APPLIANCE

[76] Inventor: Norman Erickson, 1215 Felicita La., Escondido, Calif. 92025

[21] Appl. No.: 873,430

[22] Filed: Jan. 30, 1978

[51] Int. Cl.² .............................................. A61C 17/04
[52] U.S. Cl. ...................................................... 433/93
[58] Field of Search ............................................ 32/33

[56] References Cited

U.S. PATENT DOCUMENTS

| 2,603,870 | 7/1952 | Nordin | 32/33 |
|---|---|---|---|
| 2,937,445 | 5/1960 | Erickson | 32/33 |
| 3,090,122 | 5/1963 | Erickson | 32/33 |
| 3,924,333 | 12/1975 | Erickson | 32/33 |
| 4,024,642 | 5/1977 | Zorovich | 32/33 |

Primary Examiner—Russell R. Kinsey
Assistant Examiner—John J. Wilson
Attorney, Agent, or Firm—Charles C. Logan, II

[57] ABSTRACT

A dental appliance for evacuating debris and liquid from the mouth during dental operations having a collector member and a resilient collector membrane. The collector member has a semirigid bite block portion adapted to be gripped by the molars of the patient on one or the other side of the mouth with the bite block deforming upon the initial bite of the patient so as to form a mode thereof for secure placement within the patient's mouth and which bite block portion resists further deformation permitting the patient to exert substantial pressure on the bite block portion. The collector also has a combination tongue guard and collector membrane holder formed integrally therewith. The bottom surface of the combination tongue guard and collector membrane holder is contoured to substantially conform to the inner curvature of the patient's lower arches. The combination tongue guard and collector membrane holder also has a slot therein which forms a first and a second foot member on the opposite sides of the slot. The resilient collector membrane is frictionally held within the slot with the major portion of the membrane extending therefrom.

11 Claims, 4 Drawing Figures

DENTAL APPLIANCE

BACKGROUND OF THE INVENTION

The invention relates to a dental appliance and more particularly to a device for collecting solid debris, for preventing debris from falling into the throat (oral pharynx) even when the patient is placed in a supine position, and removing liquid from the mouth of the patient during the conduct of dental operations therein.

In the past, saliva pumps (water pumps) have been used for removing liquid from the mouth of the patient during the conduct of dental operation. These pumps were perfected in the late 1900's and have for many years been a part of the dental operatory unit. In recent years a far more efficient system, the "high velocity vacuum" (an air pump) has been introduced to the dental profession. Although this system is highly efficient, it has several major drawbacks. First of all, the long life dependable system is very expensive. Secondly, the system is objectionable unless the air pump can be placed outside the confines of the dental office since it is very noisy and many medical-dental buildings do not lend themselves to this type of installation. Thirdly, until the advent of the Erickson VacEjector described in U.S. Pat. No. 3,090,122, the use of high speed vacuum for evacuation required the service of a full time chairside assistant to hold the aspirator pipes. As a consequence of the three reasons recited above, only a relatively small percentage of dental operatories are equipped with a high velocity vacuum system and some of these are not in use, or are frequently not used because of noise, lack of help or mechanical failure.

By contrast, virtually every dental operatory in the world is equipped with a saliva pump. Even in the case of most modern and recently constructed dental facilities with custom made units, a saliva ejector line is present, connected to either water or air pump.

The saliva pump with its attached saliva ejector is a very inefficient device. It is present in almost every operatory since it normally comes as part of the equipment at very little added cost and because it is better than nothing. The saliva pump is inefficient for dental evacuation because it moves only a relatively small volume of air or liquid per unit of time, as contrasted with the air pump which used a great volume of air to sweep up liquids which are near any orifice of the system's oral appliance or aspirator pipe.

Also in the case of the saliva pump, any or all orifices to the systems saliva ejector must be immersed in the liquid to be evacuated. If air can enter the system through any orifice, only air will be evacuated. If the orifice to the saliva ejector (where only one exists) is occluded, a very high vacuum is created which results in severe injury to tissues if tissue take up is the cause of occlusion. Consequently, for almost a hundred years, saliva ejectors to be used with the saliva pump have been designed with initial considerations toward eliminating tissue injury by using multiple orifices, rubber tips, slots for air relief, etc. Further progress was made by attempts to keep the tongue out of the area of operation by adding a tongue blade, curls of plastic tubing, and the like, all of which were helpful in improving a bad situation. A major drawback to these prior systems, however, was that evacuation was only partial and that the patient needed to be seated in near upright position. When it came to the point of maintaining an absolutely dry field for placement of filling materials, fluoride treatments, plastic sealants and the like, the operator had to resort to using cotton rolls, gauze sponges, or the like.

Attempts have been made to devise an instrument which would overcome or compensate for the deficiencies of the saliva pump. The inventor himself began working on the problem in the early 1950's. His first solution was a device disclosed in U.S. Pat. No. 2,937,445 which unfortunately was limited in its function and subject to the same failure as were all the contemporary and earlier devices designed to be used with the saliva pump. In the late 1960's the inventor again turned his attention to the task of trying to create an appliance which would make the saliva pump a truly viable evacuating system. The results of these efforts is disclosed in U.S. Pat. No. 3,924,333. This dental appliance, although having merit, suffers from a design that is too complex and it is subject to the many deficiencies all appliances used with the saliva pump has experienced to date The basic problem that all the inventors have been tackling since the saliva pump was perfected has been the removal of saliva. However, saliva is generated by all healthy humans. It is necessary for the health and comfort of all the tissues, hard and soft, of the oral cavity and pharynx. It has been the advent of the high speed drill and the washed field technique which relies on copious amounts of coolant and wash water to be introduced into the area that is being operated on, that has created a problem. Not only does the liquid and the solid debris splash and spray about on the sensitive tissue of the soft palate and oral pharynx, they join whatever saliva the patient generates to form an unconfined "stew" that is spread all over the oral cavity. When the patient is reclined the stew gravitates into the patient's throat. The present day saliva ejector is impotent to prevent this.

It is an object of the invention to provide a dental appliance having positive means for forming a reservoir in the patient's mouth for collection of all the coolant and wash water and for directing these liquids to the evacuating orifice of the saliva ejector.

It is also an object of the invention to provide a dental appliance that would allow the patient to swallow his saliva only, thus allowing the patient to remain more comfortable as a result of saliva keeping lubricated and moist the tissues of the throat.

It is a further object of the invention to provide a dental appliance having a positive structure to control the tongue whereby it is confined to a level below and apart from the lingual surfaces of the teeth that are to be maintained dry during operations requiring the various quadrants of the mouth to be absolutely dry.

It is a further object of the invention to provide a dental appliance having positive means for the collection of induced liquids by utilization of portions of the natural anatomy of the oral cavity never before considered in design.

It is an additional object of the invention to provide a dental appliance which does not allow the passage of the liquid and solid debris into the throat.

It is also a further object of theinvention to provide a dental appliance with structure for retaining the collector membrane which requires no special adhesive, clamps, connectors, or the like.

It is an additional object of the invention to provide a dental appliance having structure for holding the membrane in the proper relation with the anatomical tissues which it contacts to form a reservoir for the collection of fluids and saliva that are generated.

It is an additional object of the invention to provide a dental appliance having an extension of a single evacuation bore so that the connecting tube from the saliva pump or other vacuum source does not come in contact with the oral tissues of the patient.

It is an additional object of the invention to provide a dental appliance having a tongue guard that can be utilized without a change in its assembly so that it can be used either from the right side or the left side of the patient to isolate and evacuate slightly more than one half of the teeth of either the right or the left upper and lower arches.

It is also a further object of the invention to provide a dental appliance whose cost makes it acceptable as a disposable item after being used by only one patient.

SUMMARY OF THE INVENTION

The dental appliance is utilized for retaining debris and liquid from the mouth during a dental operation. The dental appliance operates in the following manner. The semirigid bite block portion of the appliance is fashioned so it may be used alternately in either the right or left quadrants of the dental arches. When it is first placed between the teeth, for example, on the right side of the patient, impressions are made in the deformable bite block portion by the cusps of the teeth contacting it. The impressions made function to hold the appliance stable. When the dental appliance is reversed to the opposite side untouched surfaces on the bite block portion to be impressed by the tooth cusps of that side are presented because it is necessary to rotate the appliance in order that the tongue guard is placed in its proper relation to the opposite arch. In short, new and distinct bite tracks are presented automatically with proper placement of the tongue guard.

The combination tongue guard and collector membrane holder which is integral with the bite block portion is shaped to conform to the curve of the lower arch and contains a single bore which serves as the channel for evacuation of fluids. This bore is continuous through the bite block portion and the handle extension. The combination tongue guard and collector membrane holder has its bore separated into two halves just short of the bite block portion by a vertical slot which acts to frictionally retain the collector membrane which is precut to the proper shape.

The collector membrane has three prime functions. Firstly, it is to provide a positive water tight seal with the soft tissues it is to contact. Secondly, it is to act as a collector of all liquid introduced and/or generated in the area of the dental operation and to channel these liquids to the reservoir. Thirdly, it is to retain all solid debris.

The materials used in the dental appliance components are both excellent insulating materials which gives them the property of being instantly the same temperature as the tissues they contact. Consequently, no tissue shock or patient reaction results. Polystyrene is eminently successful for the collector member. The material used for the collector membrane is polyethylene foam, a sealed cell foam with a waxy surface which is both feathery soft and feathery light. Because of its internal cell construction, it has the "body" to maintain or return to its original shape and form. It is also waterproof.

When the dental appliance is inserted into the patients mouth, the portion of the collector membrane which extends out of and beyond the combination tongue guard and collector membrane holder lies in sealing contact with the soft tissues overlying the mylohyoid line of the mandible. That portion of the membrane which extends beyond in back of the tongue guard continues on a straight course for a short distance and then curves upwardly in contact with the lingual mucosa of the ascending ramus. It continues the arc past and lingual to the maxillary tuberosity as it extends forward to about the midline of the hard palate. The breadth of the membrane extends across the palate and the throat to the opposite arch. It forms a positive and water tight seal along all of its borders except for the short span between the point where it emerges from the combination tongue guard and collector membrane holder to where it touches the maxillary and palatal tissue. This slightly elevated span is present so that the spray and splash of liquids as they fall upon the tissues of the teeth, palate, and collector membrane run together and course down the membrane to a point where the membrane lies about one centimeter below the level of the crest of the mandibular arch. There the arch acts as a dam to retain the fluids for evacuation. This reservoir is about a centimeter deep and two centimeters broad, bounded by the area between the notched end of the combination tongue guard and collector membrane holder and the point where the collector membrane turns up in its ascent to the palate. The reservoir concept is a creation to compensate for the limitations of the saliva pump which, to function efficiently, must be presented with no opportunity to evacuate air instead of liquid. This invention gives the saliva pump no means to dissapate its efforts.

Applicant discovered that a dental appliance which places the collecting membrane below the level of the retromolar area and in contact with tissues which are essentially vertical in relation to the plane of the collector membrane creates a reservoir which becomes the low point to which all fluids present and induced would drain regardless of whether the patient was nearly upright or nearly supine. Also important is the fact that the action of the tongue when the patient swallows, causes the collector membrane to rise and fall only a few millimeters. Since the collector membrane lies essentially at a right angle to the tissue it contacts and slides upon, and since those tissues lie in an essentially flat plane, the tissue contact is not lost and the collection reservoir remains unimpaired in function.

When the collector membrane is positioned in the slot of the combination tongue guard and collector membrane holder, the evacuating bore and orifice is divided so that the opening which is topside when placed to evacuate the right quadrants becomes nonfunctional on the tongue side when the appliance is reversed and placed to evacuate the left. The nonfunctional opening is made so by the tongue which effectively occludes it but no tissue injury can result since no buildup of vacuum can occur. The functional topside opening provides continuing relief.

During the time while liquidsare being evacuated from the reservoir formed by the collector membrane, saliva in the area of the tongue and throat serves to maintain those tissues in a lubricated and comfortable condition. Any excess saliva is swallowed by the patient, which exercise is made easy by pressure of the teeth on the bite block portion.

If the operation subsequently requires a "dry field" state as in the placement of filling material or if the operation entailed only a "dry field", it may proceed without change of armamentarium. The teeth of either the upper or lower quadrant may be washed and dried and a cotton roll placed to block Stenson's duct. The dry field can be maintained as long as necessary with the patient remaining comfortable. The tissues of the throat, in particular, remain as in the normal state, lubricated and moist.

Duringthe course of any of the previously described dental procedures, solid debris, which is retained by the collector membrane can be removed at any time with an aspirator pipe if it is available.

In addition to its function of collecting and evacuating liquids, collecting solid debris, isolating and maintaining a dry field, this appliance virtually assures that small instruments, extracted teeth dropped, cast fillings or crowns, pieces of debris such as old fillings, pieces of teeth, and the like, cannot be lost into the throat where they might be swallowed, or worse, aspirated.

DESCRIPTION OF THE PREFERRED EMBODIMENT

Figure 1:
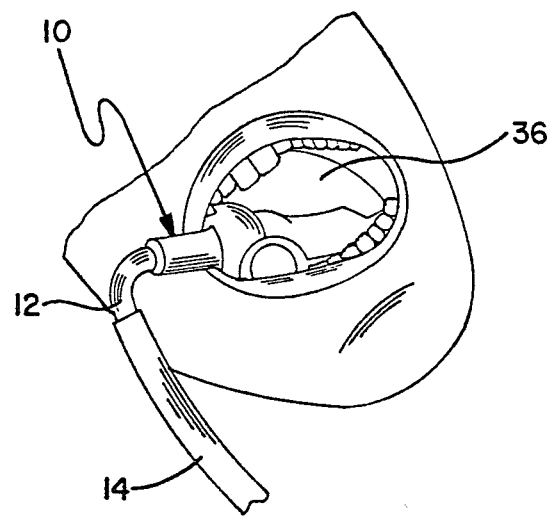
FIG. 1 is a perspective view of the dental appliance shown in a patient's mouth.

The dental appliance is illustrated in FIG. 1 in a patient's mouth and it will be identified by the term collector member which has been generally designated numeral 10. Elbow member 12 has its one end inserted into connecting tube 14.

Figure 2:
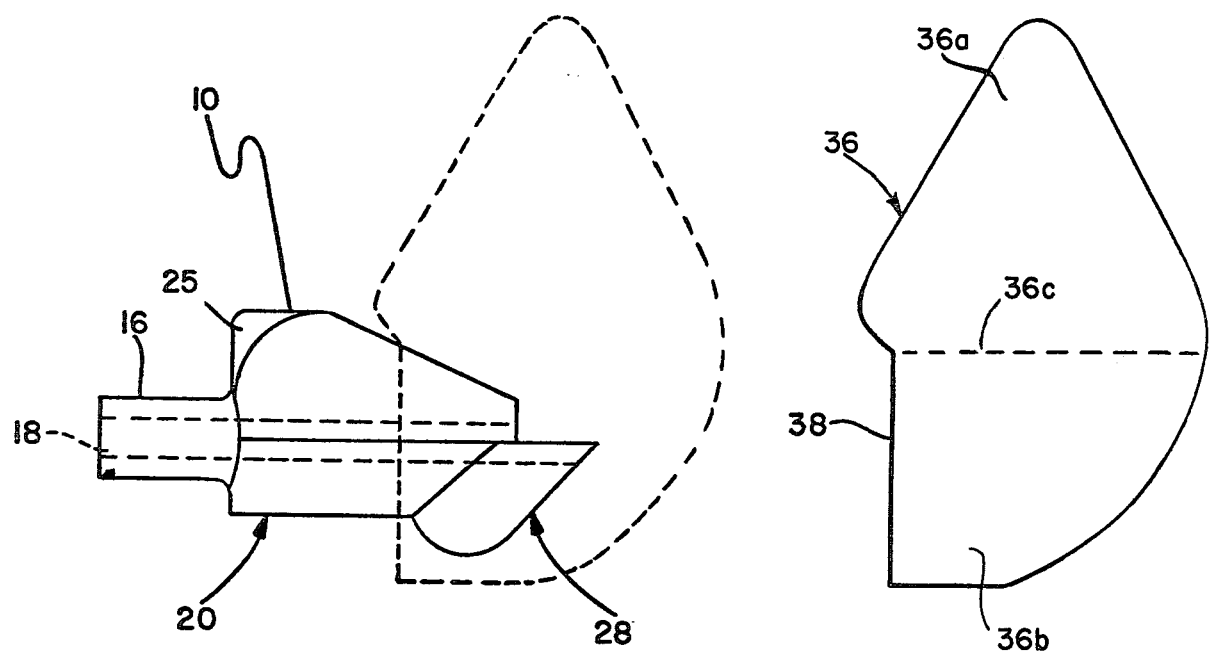
FIG. 2 is an exploded side elevation view of the dental appliance.
Figure 3:
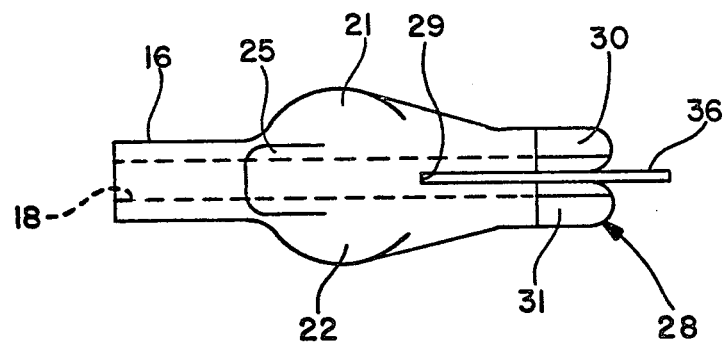
FIG. 3 is a top plan view ofthe dental appliance.
Figure 4:
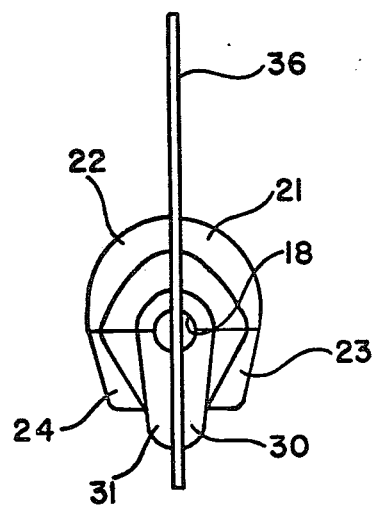
FIG. 4 is a front elevation view of the dental appliance.

The detailed structure of the collector member is best illustrated in figures 2-4. The collector member 10 has an extension member or handle 16 so that the connecting tube from the saliva pump or other vacuum source does not come into contact with the oral tissues of the patient. This eliminates the need to sterilize the vacuum connector. Also the extension serves as a handle or grip for placement or removal of the dental appliance.

Integrally formed withextension member 16 is bite block portion 20. It has a convex upper right side surface 21 and a convex upper left side surface 22. The lower right side 23 and the lower left side 24 have a somewhat cylindrical surface. Bite block portion 20 also has a ridge 25 formed along its top rear surface.

A combination tongue guard and collector membrane holder 28 is formed integrally with bite block portion 20. It has a vertical slot 29 that divides member 28 into right foot portion 30 and left foot portion 31. The vertical slot functions to frictionally hold the collector membrane 36 in position with its flat surface 38 functioning to align the collector membrane in the slot. The collector membrane is contoured to circumferentially seal the mouth of the patient into a forward and rear compartment in the manner previously described. The collector membrane when placed into its functional position within the patient's mouth is essentially folded across its length in a concave fashion at 36c to form a top of the mouth portion 36a and a bottom of the mouth portion 36b. Bore 18 passes through extension member 16, bite block portion 20 and combination tongue guard and collector membrane holder 28 to be in communication with the collector membrane for evacuating liquids that collect thereon.

Having thus described the invention, what is desired to be U.S. Letters Patent is;

What is claimed is:

1. A collector member having a semi-rigid bite block deforming upon the initial bite of the patient so as to form a mold thereof for secure placement within the patient's mouth and which bite block portion resists further deformation permitting the patient to exert substantial pressure on said bite block portion:

a combination tongue guard and collector membrane holder connected to said bite block portion which is captured within the patient's mouth, said combination tongue guard collector membrane holder having a top surface and a bottom surface, said combination tongue guard and collector membrane holder also having an uninterrupted slot formed therein that passes substantially vertically therethrough from said top surface to said bottom surface thereby forming a first and a second foot member on the opposite sides of said slot;

a resilient collector membrane having a thickness substantially as wide as said slot formed in said combination tongue guard and collector membrane holder so that said resilient collector membrane is frictionally removably held within said slot between said first and second foot members, said membrane when placed into its functional position within the patient's mouth is essentially folded in a concave fashion across its length to form a top of the mouth portion and a bottom of the mouth portion, the peripheral contour of the bottom of the mouth portion forms a sealing contact with the soft tissues overlying the mylohoid line of the mandible, the bottom portion of the mandible forms a dam or reservoir for the collection of fluids and saliva generated, the lateral edges of the collector membrane where it is folded upwardly lies in sealing contact with tissue covering the internal walls of the ascending ramus of the mandible, and the top of the mouth portion of the collector membrane extends forwardly from the folded area over the palate where it conforms to and lies on the maxillary and palatal tisue thereby functioning to separate the mouth into a forward compartment that is being worked on and a rear compartment.

2. A dental appliance as recited in claim 1 wherein said bite block portion has a bore passing through it that communicates with said combination tongue guard and collector membrane holder, said collector membrane functioning during said dental operation to collect the fluids and saliva generated and to divert them to the bore of said bite block portion.

3. A dental appliance as recited in claim 2 wherein said bore passes through to the end of said combination tongue guard and collector membrane holder such that the collector membrane forms a wall that divides said bore into separate chambers.

4. A dental appliance as recited in claim 2 where said bore of said bite block also passes through said extension member.

5. A dental appliance as recited in claim 1 wherein said collector membrane is contoured to circumferentially seal the mouth of the patient into said forward and rear compartments.

6. A dental appliance as recited in claim 1 wherein said combination tongue guard and collector membrane holder is integrally formed with said bite block portion.

7. A dental appliance as recited in claim 1 further comprising an extension member that is connected to said bite block portion on a side opposite to the side to which said combination tongue guard and collector membrane holder is connected.

8. A dental appliance as recited in Claim 6 wherein said extension member is integrally formed with said bite block portion.

9. A dental appliance as recited in claim 1 wherein the bottom surface of said combination tongue guard and collector membrane holder is contoured to substantially conform to the inner curvature of the patient's lower arches.

10. A dental appliance as recited in claim 1 wherein said bite block portion is made of polystyrene material.

11. A dental appliance as recited in claim 1 wherein said collector membrane is made of polyethelene foam.

* * * * *